United States Patent [19]
Kuniyuki

[11] Patent Number: 5,120,660
[45] Date of Patent: Jun. 9, 1992

[54] METHOD FOR CANINE FERTILITY DETECTION

[75] Inventor: Andrew H. Kuniyuki, Berwyn, Pa.

[73] Assignee: International Canine Genetics, Inc., Malvern, Pa.

[21] Appl. No.: 446,068

[22] Filed: Dec. 5, 1989

[51] Int. Cl.⁵ .......................................... G01N 33/493
[52] U.S. Cl. ...................................... 436/65; 436/518; 436/811; 436/814; 436/906; 435/7.1; 435/21; 435/28; 435/7.9
[58] Field of Search ................ 435/7.1, 7.91, 21, 28, 435/975; 436/504, 518, 533, 536, 542, 548, 65, 87, 164, 172, 804, 806, 814, 906; 530/387, 389

[56] References Cited

U.S. PATENT DOCUMENTS 3,991,174 11/1976 Grundman
4,693,969 9/1987 Saxena et al. ..................... 435/7.94
4,880,914 11/1989 Saxena et al.

OTHER PUBLICATIONS

Boyns et al., J. of Endocrinology, vol. 55, pp. 279-291 (1972).
Wolf et al., Nucleic Acids Research, vol. 15(24), p. 1062 (1987).
Wildt et al., Chemical Abstracts, vol. 89, abstract No. 40149z (1978).

*Primary Examiner*—Sam Rosen
*Attorney, Agent, or Firm*—Howson and Howson

[57] ABSTRACT

The present invention describes methods and compositions for detecting the fertility of a canine female based on identification of certain characteristic cLH peptides and carrier proteins found in canine urine. More specifically free or complexed metabolites of luteinizing hormone (LH) are detected.

31 Claims, No Drawings

METHOD FOR CANINE FERTILITY DETECTION

The present invention refers generally to a diagnostic method for detection of the stages of fertility in a canine species. More particularly, the present invention concerns the identification of peptide fragments of canine LH in the biological fluids of a female dog.

BACKGROUND OF THE INVENTION

Canine luteinizing hormone (cLH), which in concert with follicle stimulating hormone (FSH) causes ovulation in a female dog, is a peptide hormone containing an alpha protein subunit of approximately 13,400 daltons and a beta protein subunit of approximately 18,200 daltons. The alpha subunit is shared by a number of other peptide hormones and therefore, specificity is derived from reaction with the beta subunit. D. L. Wolf et al., *Nucl. Acids Res.*, 15:10602 (1987) compared the nucleic acid and amino acid sequences of dog beta LH to that of rat, cow and human, calculating an amino acid sequence homology of 89% with rat, 84% with cow and 74% with human. Calculations based on cDNA sequences archived with GENBANK are similar to those published figures.

Detection of LH levels in the biological fluids of other mammals, particularly humans, has been employed in diagnostic procedures and processes for correlation with ovulation. These processes and products enable one to detect the timing of ovulation for purposes of avoiding or facilitating pregnancy. In humans, LH is an intact molecule which can be detected in blood and, more significantly, in urine. Thus, simple tests for the presence of LH are available for fertility detection.

In canines, however, the study of LH has not revealed its presence in urine. A radioimmunoassay has been described for the detection of cLH proteins in canine serum. However, serum testing of canines to assess the onset of the fertile period is an onerous and impractical method for dog owners and breeders to routinely perform. Thus, processes or products for routine detection of LH in canines has not been pursued as a practical method of detecting fertility.

There exists, therefore, a need in the art of canine breeding, particularly in the breeding of dogs with desirable genetic traits, for an efficient and accurate means for dog owners and breeders to determine the condition of fertility in the dog.

SUMMARY OF THE INVENTION

The present invention provides products and processes directed to the detection of fertility, and the timing of ovulation in a canine. Surprisingly, the inventors have made certain observations concerning the metabolism of canine luteinizing hormone (cLH) which enable the assays of the present invention to correlate detection of the presence of specific metabolites of cLH in canine urine with fertility.

In one aspect, the present invention provides a diagnostic method to determine the condition of fertility in a tested animal based on the detection of certain cLH metabolites present in the urine of the animal. The metabolites include one or more peptide fragments or sequences which naturally occur within the cLH protein molecule either or complexed with the protein carrier to which such fragments are attached after the hormone is metabolized and excreted in the urine of female canines during the period preceding and during ovulation.

These methods involve detecting the presence of one or more of the cLH peptides and the protein carrier by introducing into a urine sample at least one antibody capable of binding to a peptide fragment or protein carrier. The antibody is desirably associated with a label capable of producing a visually detectable signal. Other embodiments of the methods include antibodies which bind to different LH peptide sequences or to an LH peptide sequence and carrier protein and which are associated with interactive labels which provide a detectable signal of the presence of the peptides or proteins characteristic of fertility or ovulation.

Still a further aspect of the present invention provides an antibody capable of binding to a canine LH metabolite present in the urine of a female canine just preceding or during ovulation.

Yet another aspect of this invention is a diagnostic kit for the determination of the condition of fertility in a canine based on the presence of LH metabolites in urine. This kit contains one or more of the above described antibodies, and can be employed for the performance of one or more of the methods of this invention. The antibody in the kit is desirably conjugated to a detectable label. The specific antibodies described herein may also be parts of such a diagnostic kit, as well as typical buffering, washing and other diagnostic reagents conventional in such kits. Conventional components such as means for holding the urine sample, vials and the like are also included.

Other aspects and advantages of the present invention are described further in the following detailed description of preferred embodiments of the present invention.

DETAILED DESCRIPTION OF THE INVENTION

The inventors have made the surprising discovery that unlike other mammals which excrete intact LH protein in urine, canines metabolize LH, ultimately producing fragments of the LH hormone detectable in urine, among other biological fluids. The size and composition of the fragments can vary among different breeds of dogs and also from individual dog to individual dog. Although differences in the size of the cLH fragments occur in different dogs, the fragments appear to result from of one or two sites of digestion, or cuts in the cLH protein, yielding large peptide fragments. These metabolites of canine LH are occasionally detectable in canine serum at the onset of, and during, ovulation. However no peak in LH fragments has ever been detected in canine urine.

The present invention involves the detection of cLH peptide fragments in urine, coupled with the surprising determination, that such fragments are bound to a large carrier protein of approximately 110 kd in size. The cLH peptide fragments are bound in specific orientation to the carrier protein, and appear in detectable levels in canine urine immediately preceding and during the onset of ovulation.

The present invention deals primarily with an assay for detection of ovulation, which involves identification of the presence of LH metabolites and/or the carrier protein in a urine sample of the selected female animal. Thus detection of the carrier protein alone, one or more associated LH peptide fragments, or the carrier protein/associated LH peptide fragment complex in canine urine is indicative of the dog's fertile period and may permit a dog owner to appropriately time breeding of the dog.

Although throughout this specification all references to the selected animal refer to dogs, for simplicity, it should be understood that the assays taught by the present invention may also be applied to ovulation detection in cats, and other animals, where the metabolism of the LH hormone and its association with a large carrier protein is similar to that of canines.

The present invention employs these unique observations in assay methods for detection of the peptides, the carrier protein, or more desirably, the carrier/peptide complex. This invention responds to a need in the field of breeding such animals, as well as provides a simple test for use by animal owners. The method and products provided by this invention have a number of advantages in contrast to present methods for detecting the onset of ovulation in animals.

Detection of a substance in urine as opposed to substances which must be obtained from serum is a clear advantage both for at home use by non-veterinarian or non-medical persons as well as for clinical use. The collection of urine does not involve an invasive procedure such as the collection of a blood sample. Thus the method and products associated therewith may be easily used by persons having no special clinical training. The presently available ovulation tests for certain animals, particularly dogs and cats, are designed for administration by a veterinarian.

In the practice of the method of this invention, a variety of assay formats may be employed which use one or more antibodies capable of binding to antigenic regions on the LH peptide metabolites or the carrier protein in the urine of dogs, including those described in the examples below. According to one embodiment of this invention a method for detecting fertility in a female dog employs an antibody capable of binding to an epitope on one or more of the cLH peptide fragments which are in the canine urine. In another embodiment a method for detecting fertility in a female dog employs an antibody capable of binding to an epitope on the carrier protein. A most preferred embodiment provides for the use of more than one antibody, e.g., a first antibody capable of binding to a selected LH fragment and a second antibody capable of binding to the carrier protein.

These methods may take advantage of a number of well-known immunoassay methodologies which employ antibodies for detection of specific peptide or protein substances. Such assays may include, for example, the use of at least one labeled antibody to detect one or more individual LH peptide metabolites in the urine sample. Alternatively, an assay may use one or more labeled antibodies capable of binding to one or more epitopes on the carrier protein. Still another alternative assay employs both an antibody to detect a selected LH peptide as well as an antibody to bind to the carrier protein.

The advantage of using the carrier protein as a target in a diagnostic method of fertility is its very large size, approximately 90 to 110 kd, which provides multiple sites for binding by several different monoclonal antibodies (Mabs). Multiple binding amplifies the signal as a result of increasing the number of available enzymes in the reaction. This aspect of the carrier protein thus enables the use of sandwich assays, among others, which are characterized by increased sensitivity to detection of the presence of carrier protein in the urine.

The antibodies to cLH peptides or to epitopes on the carrier protein for use in the assays of this invention may be polyclonal. However, it is desirable for purposes of increased target specificity to utilize monoclonal antibodies (Mabs) in the assays of this invention. Additionally synthetically designed monoclonal antibodies may be made by known genetic engineering techniques and employed in the methods described herein. For purposes of simplicity the term Mab(s) will be used throughout this specification; however, it should be understood that certain polyclonal antibodies and recombinant antibodies may also be employed in place of Mabs in the below described assay formats.

For use in the assays of the invention, any Mab generated by the now well-known Kohler and Milstein techniques and modifications thereof and directed to an epitope on the carrier protein, which is not involved with binding to the cLH fragments, may be employed. The only requirement for selection of the appropriate Mab for use in the practice of this invention is that, where more than one antibody is provided, the antibodies must be selected which are capable of binding at a sufficient distance from each other on the LH peptide(s) and/or carrier protein so as to prevent steric hindrance. The following examples describe the use of Mabs generated to bind to the carrier protein. However, the invention is not limited to specific Mabs, since other Mabs may be generated by one of skill in the art to appropriate epitopes of the carrier protein given the teachings of this invention.

Similarly, Mabs directed to the cLH fragments may be generated for use in this invention. The specific monoclonals CLH1B1, CLH1C3, CLH1D1, CLH1D5 and CLH1D6 have been generated employing the cLH peptide region 87-110. Similarly, the monoclonals, CLH2A3 and CLH2A5, have been generated to the immunogen of the cLH peptide region 11-23. These monoclonal antibodies are described below. One of skill in the art may generate any number of cLH Mabs useful in this assay by using fragments of cLH as an immunogen and employing the teachings herein. This invention is not limited to use of the specific Mabs to cLH described below.

Although the antibodies employed in these methods may be associated with individual labels, where more than one antibody is employed in the method, the labels are desirably interactive to produce a detectable signal. Most desirably the label is detectable visually, e.g., colorimetrically.

Detectable labels for attachment to the antibodies useful in the assays of this invention may also be easily selected by one skilled in the art of diagnostic assays. Labels detectable visually are preferred for use in diagnostic "at-home" kits and even in clinical applications due to the rapidity of the signal and its easy readability. For colorimetric detection, a variety of enzyme systems have been described in the art which will operate appropriately in the homogenous assay, described below. As one example of enzyme 1, glucose oxidase may be employed which uses glucose as a substrate. Interaction between glucose and glucose oxidase releases peroxide as a product. Enzyme 2 may therefore be peroxidase, which reacts with peroxide and a hydrogen donor such as tetramethyl benzidine (TMB) producing an oxidized TMB that is seen as a blue color.

In the assays employing colorimetric enzyme systems, such as horseradish peroxidase (HRP) or alkaline phosphatase (AP), the reaction should be read within approximately 5 to 15 minutes, preferably 10 minutes, to obtain an accurate result. A longer reaction time can lead to color changes induced by trace amounts of enzyme remaining on the reaction surface. Where desirable, a "stop" solution can be employed to disable the enzyme from further reaction after the above 5 to 15 minute period. It is known, for example, that sulfuric acid may be added to stop the reaction of HRP. However, the acid causes a change in color from blue to yellow.

A "stop" solution for HRP may include about 20 mM sodium azide, made in 0.25 M sodium acetate to a pH of about 5.0. About 0.2 to about 0.5 mls of this solution added to the sample containing HRP after about 10 to 15 minutes, stops further reaction of HRP, retaining the blue color or no color in the assay sample indefinitely.

A "stop" solution for AP includes 0.1 M tetrasodium ethylene diamine tetraacetic acid, adjusted to a pH of approximately 7.0 with phosphoric acid. When added to the assay sample following the 5 to 15 minute reaction time, this solution stops further reaction of AP with its substrate indoxyl phosphate, also retaining indefinitely the color, or lack thereof, indicating a positive or negative test result.

Other such proximal enzyme systems are known to those of skill in the art, including hexokinase in conjunction with glucose-6-phosphate dehydrogenase which react with ATP, glucose, and AND+ to yield, among other products, NADH that is detected as increased absorbance at 340 nm wavelength. The loss of absorbance at 340 nm wavelength by the oxidation of NADH is another indicator of positive results in either allosteric activation using phosphofructokinase in conjunction with phosphoenol pyruvate carboxylase and substrates fructose-6-phosphate and NADH or allosteric inhibition using aspartate aminotransferase in conjunction with phosphoenol pyruvate carboxylase and substrates oxalacetate, glutamate and NADH. Also, bioluminescence or chemiluminescence can be detected using, respectively, AND oxidoreductase with luciferase and substrates NADH and FMN or peroxidase with luminol and substrate peroxide.

Other label systems that may be utilized in the methods of this invention are detectable by other means. For example, one desirable method employs colored latex microparticles, such as those marketed by Bangs Laboratories of Indiana. These latex particles in which is embedded a dye may be used in place of enzymes to form conjugates with the antibodies and the peptides in the methods of this invention and provide a visual signal indicative of the presence of the resulting "sandwich" in applicable assays. The use of such particles eliminates the need for subsequent substrate addition steps, and avoids enzyme and substrate reagent instability.

Other conventional label systems that may be employed include fluorescent compounds, radioactive compounds or elements, or immunoelectrodes. These and other appropriate label systems are known to those of skill in the art.

As one illustration the method of this invention is embodied in the following homogeneous enzyme immunoassay employing two Mabs directed against the carrier protein and an LH peptide sequence, respectively. Alternatively the two Mabs could be directed against two different epitopes on the large molecular weight carrier protein. Briefly, the first Mab is preferably conjugated to a first enzyme (enzyme 1). A second Mab directed against a different epitope is preferably conjugated to a second enzyme (enzyme 2) which, in proximity to enzyme 1, is capable of producing a color reaction.

According to this embodiment of an assay of this invention, a urine sample from a female dog is combined in a test tube or other container with both labeled Mabs. A color appears only when the urine sample contains cLH bound to the carrier, because the enzymes are brought into close proximity due to side-by-side binding of their antibody conjugates to the carrier and cLH fragment. The product released by enzyme 1 reaction can be utilized immediately by enzyme 2 to convert the enzyme 2 co-reactant into a colored product capable of visualization. If the two enzymes are not in close proximity, the second reaction does not have a sufficient concentration of product 1 to proceed in generating sufficient colored product to be visible.

However, this homogeneous assay of this invention is limited to the use of only those Mabs binding to adjacent epitopes of the cLH fragment attachment site which do not sterically hinder either the Mab against the cLH fragment or other adjacent site carrier protein Mabs.

Another assay format employing the antibodies of this invention is performed as follows: one antibody directed to a first selected epitope on the carrier protein is conjugated by conventional means to a conventional solid matrix, such as latex beads. A second antibody directed to a second epitope on the carrier protein or to an associated LH peptide sequence is conjugated again by conventional means to a selected enzyme or colored latex microparticle. According to this assay a sample of urine from a female dog is incubated with the first Mab and the latex beads. The beads are then collected generally by trapping the beads by size or charge, and separating the beads to which carrier protein/LH peptide from the urine is now attached via the first antibody from the urine sample. The second Mab is then added to the beads and allowed to react with the carrier protein or LH peptide bound to the first Mab on the beads.

After an appropriate reaction time, generally 2 to 30 minutes, the beads are washed. Where colored latex conjugates are employed, simple washing alone is sufficient to either remove the microparticles therefrom in the absence of cLH in the urine. If the microparticles remain after the washing, due to their binding in an immunological sandwich with the cLH fragment and antibody, the dye in the microparticles remains, thus providing visual indication and confirmation of fertility on the reaction surface. Alternatively, where enzyme conjugates are employed in this system, the beads are washed and a substrate capable of reacting with the enzyme label is added to the beads. In the presence of the substrate any of the second enzyme labelled antibody which has bound due to the presence of carrier protein or LH peptide sequence in the urine sample will react with the substrate and turn the sample blue.

Lack of color in either embodiment after washing (and substrate addition, where indicated) indicates that no carrier protein or LH peptide was present in the urine and the dog that contributed the urine sample is not nearing the onset of ovulation.

An alternative assay employing two or more Mabs to different epitopes on the carrier protein or on selected LH peptide sequences includes a variation of the above assay in which the solid phase matrix, e.g. latex beads, are bound to a solid surface and the urine is poured over the beads. This type of assay eliminates the need for collection of the beads and separation of the urine. Other than these modifications the remaining steps as described immediately above may be performed.

Still a further variation of a diagnostic assay employing two or more antibodies of this invention is a latex agglutination assay. Such an assay is known to one of skill in the art and may be briefly described as follows. Two or more Mabs directed to different epitopes on the carrier protein and/or LH peptides are bound to different solid matrices, e.g. different latex beads. Both beads are together in solution, and the urine sample is added to the solution. Standard Brownian motion keeps the beads in solution. By controlling the concentration of the beads to the amount of urine, in the presence of the carrier protein/LH peptide in the urine, the beads having different Mabs will form a lattice network with the carrier protein/LH peptide complex. The resulting agglutination or clumps of Mabs-bound beads bound to two or more sites on the complex are thus capable of visualization in a conventional test tube or on a slide.

Additionally, assays may be performed which only utilize a single Mab capable of recognizing the native LH peptide or carrier protein in urine. Most preferably a classical competition assay format may be employed. Alternatively an indirect immunoassay employing one Mab to the carrier protein or selected LH peptide sequence may be employed.

An exemplary competitive immunoassay may employ synthetically generated cLH peptides. In this case, a peptide (e.g., peptide #3 as described below) capable of reacting with a selected anti-cLH antibody (e.g., LH3 as described in the examples below) will be conjugated to HRP or colored latex microparticles. LH3 will be conjugated to a solid surface, such as latex particles or a dipstick. The peptide 3-HRP conjugate will compete for binding to LH3 with cLH present in samples tested. Color develops or remains in the absence of cLH.

A single Mab to native cLH, conjugated by conventional means to a solid matrix such as latex beads is reacted with 1 ml of urine for 10 minutes. A drop (approximately 50 μl) of synthetic cLH peptide fragment conjugated to either HRP or colored latex microparticles is added and incubated for an additional 5 minutes. The beads are then collected generally by trapping the beads by size or charge, and separated. If native cLH peptide is present in the urine from a fertile or ovulating animal, the native LH peptide is now attached to the beads via the Mab. In the case of a urine sample from a non-ovulating animal which is devoid of native LH peptide, synthetic cLH peptide HRP conjugate or colored latex microparticle conjugate is now attached via the Mab specific for the this cLH fragment. The collection surface is washed with 1 ml of wash reagent and 0.2 ml of TMB/urea peroxide is added. After 5 minutes, 0.2 ml of stop reagent is added. A blue color develops with the peptide enzyme conjugate or remains with the peptide colored latex conjugate in the absence of the cLH peptide and, therefore, a positive test remains clear. This competition assay can also be conducted with the latexMab conjugated spotted on a membrane or surface of commercial devices such as those manufactured by Pall Corporation, Porex, or Bio Rad, or with the Mab spotted on a dipstick. In these cases, the urine sample and cLH fragment HRP conjugate (or colored latex microparticle conjugate) are added in sequence following the same reaction time protocol. The dipstick incubations can be performed in a test tube.

An exemplary indirect assay employing one Mab is described as follows: 100 microliter of urine is passed through nitrocellulose membrane of 3 to 5 micron porosity. Any LH peptide or carrier protein in the sample binds non-specifically to the membrane. After 1 minute to allow adsorption binding, 0.5 ml of blocking solution is added and incubated for 2 minutes to block the remaining non-specific binding sites on the membrane. This is followed by 0.5 ml of Mab to the LH peptide or carrier protein conjugated to HRP and diluted in blocking buffer. The Mab-HRP conjugate is incubated for 10 minutes. This labelled Mab will bind to any LH peptide or carrier protein bound to the membrane. The potential signal is amplified with goat anti-antibody IgG conjugated with HRP in a 1:1000 dilution in the blocking buffer and incubated for 5 minutes. This anti-antibody will bind to the bound Mab and thus amplify the label. The membrane is washed with wash reagent and 0.2 ml of TMB/urea peroxide is added. After 5 minutes, stop reagent is added. A blue color change indicates the presence of LH peptide or carrier protein in the urine sample.

These and other assay formats employing one or more Mabs are known to one of skill in the art for diagnosis of many types of conditions. Thus, the present invention also encompasses alternative enzyme immunoassays utilizing the Mabs against the carrier protein and cLH fragments. Variations of these described assays and other known assays may be employed in the method of this invention.

The methods and Mabs described herein may be efficiently utilized in the assembly of a diagnostic kit, which may be used by pet owners and breeders. Such a diagnostic kit contains the components necessary to practice one or more of the assays described above for the detection of the LH peptide fragments in association with the carrier protein in dogs. Thus, for homogeneous assays the kit may contain a first Mab directed to a first epitope on a selected LH peptide fragment or first epitope on the carrier protein, which Mab is associated with a first enzyme, a vial for containing the urine sample, and a second Mab conjugated to the second enzyme, which in proximity to the first enzyme, produces a visible product. Other conventional components of such diagnostic kits may also be included.

Alternatively, a kit may contain a Mab directed against a selected LH peptide fragment and/or the carrier protein bound to a solid surface and associated with a first enzyme, a different Mab associated with a second enzyme, and a sufficient amount of the substrate for the first enzyme, which, when added to the urine and Mabs, provides the reactant for the second enzyme, resulting in the color change.

For an agglutination assay kit, the Mabs directed against different epitopes on the carrier protein, different LH peptides, or to both the LH peptide fragment and the carrier protein as a complex would be provided bound to the latex beads.

Where the detectable label present in association with the antibody is designed for non-visual detection, e.g., for radioimmunoassay, the standard components necessary for this assay, e.g., controls, standards and the like are included in the kit.

In the diagnostic kits of this invention, reagents are included which define a clear cut end to the color development step, such as the stop solutions described above.

The following examples illustrate the practice of the present invention, including the development of presently preferred Mabs, and various assay methods. These examples illustrated the invention only, and are not limiting thereof.

EXAMPLE 1

Detection of cLH Fraqments and Carrier Protein in Canine Urine cLH rich samples from five dogs were subjected to molecular sieving through a TSK G2000 high protein liquid chromatography (HPLC) column and the column fractions were assayed with the dot blot procedure. If cLH remained intact as a dimer, the expected molecular weight would be 31,600 Daltons and a free beta subunit would be 18,200 Daltons. If the cLH was metabolized into smaller fragments, the signal should appear in the fractions representing material less than 18,200 daltons in size.

Surprisingly, cLH eluted in the high molecular weight fractions (greater than 100,000 daltons), not in the low molecular weight region as expected. The results were consistent with each dog. Subjecting the HPLC fractions to sodium dodecyl sulfate polyacrylamide gel electrophoresis (SDS PAGE) demonstrated that the cLH rich fractions contained a predominant protein of approximately 100,000 daltons. The fractions did not have enough material to observe any band in the lower molecular weight region where cLH is expected to appear.

Therefore, the same urine samples were concentrated, molecular sieved through Bio Gel P200 liquid chromatography, fractions were dot blot assayed and subjected to SDS PAGE. The same dot blot results were observed. The cLH rich fraction eluted in the large molecular weight region. In this procedure sufficient material was present to observe bands corresponding to cLH. The dot blot assay demonstrated a gradient in signal intensity quickly forming a sharp peak and then tailing off. The only bands in the silver stained SDS PAGE electropherograms corresponding to this gradient pattern appear in the low molecular weight region with sizes ranging from 6900 to 9100 daltons.

Further evidence that these are the true cLH fragments is provided by the observation that these fragments usually appear in pairs and the sum of their molecular weights approximates 18,000 daltons, the size of the beta subunit.

These small molecular weight fragments could appear in the large molecular weight fractions of two molecular sieving techniques only if they are attached to the large molecular weight protein found in the same fraction, or, alternatively, they polymerize yielding an entity always greater than a 12-mer. The second possibility is unlikely since polymerization usually results in intermediate sizes which should have been detected in other molecular weight fractions by the dot blot assay. Intermediate sizes have never been observed.

Therefore, it is presently determined that the fragments are attached to the large molecular weight protein which serves as a carrier and which is always present in cLH rich fractions. The apparent molecular weight of the carrier protein as determined by SDS PAGE ranges from approximately about 90,000 to about 110,000 daltons.

EXAMPLE 2

Generation of anti-cLH Peotide Mabs

To generate usable reagents for an enzyme immunoassay, four peptides overlapping amino acid region 87 to 110 of the published cLH sequence [see Wolf et al, cited above]: Ser Cys Arg Cys Gly Pro Cys Arg Leu Ser Asn Ser Asp Cys Gly Gly Pro Arg Ala Gln Ser Leu Ala Cys were generated and are identified below as Peptides #1-4. One peptide representing region 11 to 23 was also generated and is identified below as Peptide #5. These peptides were selected after hydropathy analysis which indicated potentially antigenic zones.

These selected peptides were synthesized by conventional methods. The size of the cLH fragments observed in Example 1 suggested that the probable cleavage site resided somewhere close to the center of the beta subunit. These five peptide regions identified below represent each fragment generated by a cleavage at the center of that subunit.

Peptide #1: Ser Cys Arg Cys Gly Pro Cys Arg Leu Ser Asn Ser Asp Cys

Peptide #2: Ser Cys Arg Cys Gly Pro Cys Arg Leu Ser Asn Ser Asp Cys Gly Gly Pro Arg Ala Gln Cys Peptide #3: Ser Cys Arg Cys Gly Pro Cys Arg Leu Ser Asn Ser Asp Cys Gly Gly Pro Arg Ala Gln Ser Leu Ala Cys Peptide #4: Cys Arg Leu Ser Asn Ser Asp Cys Gly Gly Pro Arg Ala Gln Ser Leu Ala Cys Peptide #5: Pro Ile Asn Ala Thr Leu Ala Ala Glu Asn Glu Ala Cys Mabs were developed which are specific to cLH and characterized by high sensitivity as a result of high affinity to the synthetic cLH peptides described above. These Mabs were developed using standard laboratory mice in the now traditional Kohler and Milstein techniques with modifications known to one of skill in the art for the generation of Mabs. The Balb/C mice were injected with 10 μgs of the pooled peptides Nos. #1 through #4, or simply the peptide #5. For each injection the pooled peptides or the single peptide #5 were conjugated to a different carrier, either latex particles or the carrier proteins, keyhole limpet hemocyanin or bovine thyroglobulin, to minimize a response to the carrier employed. The mice were sequentially boosted with the same peptide attached to different carriers to stimulate the cells to preferentially reognize either the pooled peptides, spanning cLH region 87-110, or peptide #5, spanning cLH region 11-23, as the target.

In the generation of Mabs for use, two regimens were followed. In one regimen, the mice were boosted every other day for approximately 3 weeks to obtain Mabs directed to the selected peptide. Alternatively, to obtain higher affinity Mabs other mice were boosted approximately every two weeks for 3 months to generate antibodies selected to the peptides presented. The binding ability of the antibodies in the animals was examined by binding the peptides to microtiter plates, exposing the plates to dilutions of the animal's serum, and obtaining titers greater than 1:50,000 through 1:100,000.

According to conventional methods, spleen cells from responsive mice were fused with the murine myeloma cell line, SP2/0, to produce hybridoma cell lines secreting Mabs responsive to cLH region 87-110 or cLH region 11-23. At present five Mabs have been developed which bind cLH 87-100, and are designated CLH1B1, CLH1C3, CLH1D1, CLH1D5 and CLH1D6.

Two monoclonals, CLH2A3 and CLH2A5, have been developed which bind cLH peptide 11-23.

EXAMPLE 3

Generation of anti-Carrier Protein Mabs

Monoclonals capable of binding to epitopes on the cLH carrier protein are generated in the same manner as described above in Example 2 for the cLH peptides. The immunogen for use in developing these anti-carrier Mabs is obtained by concentrating canine urine samples rich in cLH fragment-carrier protein complexes (see Example 1) using the Centricon 10 centrifugal concentrator [Amicon, Danvers, MA]. One to two ml samples of this 10-fold concentrated urine are chromatographed through Bio Gel P200 chromatographic column (1cm×30cm) [Biorad, Richmond, CA], using an elution buffer containing 0.15M NaCl, 10 mM Tris, pH 7.5, and 0.01% by weight thimerosal as a bacteriocide.

The cLH-carrier protein complexes in the urine is extracted in the first eight 1 ml fractions, as detected by dot blotting. However, the first four dot blot positive 1 ml fractions are pooled and employed as the antigen for the carrier protein.

Mabs to this carrier protein are developed and assayed for binding ability by following the protocols described above in Example 2, except substituting the pooled fractions as antigen and binding the pooled target to the plates for the serum dilutions. Mabs generated in this manner are capable of binding to the carrier protein, and may be employed in the assays of this invention.

EXAMPLE 4

Developing Immunoassay Reagents

The Mabs directed to the epitopes on the cLH protein (Example 2) or on the carrier protein (Example 3) are useful as reagents assays of this invention for identifying ovulation in an animal. One or more of these Mabs may be employed to identify and bind to one, or desirably, multiple antibody binding sites on the cLH-carrier protein complex in the urine of a tested animal to enhance the detection thereof.

To generate appropriate reagents, the Mabs of this invention are desirably attached to a label by conventional methods known to one of skill in the art for use in the assays of this invention. The preferred method for attaching an enzyme label (HRP or AP) to the Mab uses the heterobifunctional conjugation agent, sulfosuccinimidyl 4-(N-maleimidomethyl)cyclohexane-1-carboxylate, (SMCC) in the following manner:

4 mg of Mab are equilibrated in 0.1 M sodium phosphate buffer, pH 6.0 by chromatography through an excellulose column (manufactured by Pierce). Fractions containing the Mab are concentrated to 0.45 ml in a centricon 10 (manufactured by Amicon) by centrifugal concentration. 50 ul of 0.1 M 2-mercaptoethylamine in 0.1 M sodium phosphate buffer, pH 6.0 are added and incubated for 1.5 hours at 37.C. The reduced Mab is then equilibrated in 0.1 M sodium phosphate, 5 mM EDTA, pH 6.0 through excellulose chromatography and concentrated to 0.5 ml in a centricon 10. 4 mg of HRP are equilibrated in 50 mM sodium borate, pH 7.6 by chromatography through an excellulose column.

Fractions containing the HRP are concentrated to 0.5 ml by centrifugal concentration in a centricon 10.1 mg of SMCC is added and incubated for 30 to 60 minutes at 30.C. The SMCC labelled HRP is then equilibrated in 0.1 M Tris buffer, pH 7.0 through excellulose chromatography and concentrated to 1 ml using a centricon 10. The SMCC labelled HRP is then combined with the reduced Mab and incubated for 20 hours at 4° C. 10 ul of 0.1 M 2-mercaptoethylamine in 0.1 M sodium phosphate, pH 6.0 is added and incubated for 20 minutes at room temperature.

The Mab-HRP conjugate is fractionated through Sephadex G-200 chromatography in 0.15 M sodium chloride, 10 mM Tris, 0.01% thimerosal, pH 7.5 and stored at 4° C. Other conjugation methods include one- or two-step glutaraldehyde method, periodate-oxidation method, water soluble carbodiimide method, homobifunctional imidoesters, hydroxysuccinimide esters, or maleimide methods, other heterobifunctional hydroxysuccinimidyl ester, maleimide, pyridyl disulfide or active halogen reaction methods, photoreactive phenyl azide methods, and avidin-biotin methods.

These conventional methods are also useful in conjugating the peptides to enzyme labels for the development of competition assay reagents. For the examples listed above, the peptides are substituted in place of the Mabs and are concentrated by precipitation with ethanol instead of by centrifugal concentration using the centricon 10.

It is understood by one of skill in the art, however, that the present invention is not limited to the specific Mabs or Mab-label conjugates described by the Examples 2-4 above, since other Mabs may be easily generated by one of skill in the art according to the teachings of the present invention.

EXAMPLE 5

Homogeneous Assay for Fertility Detection

According to the homogeneous assay of this invention, 1 ml of urine is added to a test tube followed by a drop (50 ul) of antibody conjugate reagent. Antibody conjugate reagent is described as 10 ug/ml each of the Mab against the first cLH fragment, PEPTIDE #2 conjugated to glucose oxidase and the Mab against the carrier protein conjugated to HRP. Also added to the test tube are 2 drops (100 ul) of glucose-TMB reagent (20 mM of each in 500 mM Acetate buffer pH 6.0), and the solution is mixed thoroughly. After 10 minutes, 2 drops (100 ul) of stop reagent (100 mM Azide in Acetate buffer) are added and mixed thoroughly. The presence of cLH is noted by the development of a blue color.

Canine urine tends to have particulates about 1 to 5 microns in size which clog collection devices. This is a variable condition but one that will stop further steps in the performance of immunoassays requiring liquid absorption into blotter pads or reservoirs. This homogeneous assay of the invention overcomes this by avoiding the need to absorb excess liquids. It also has the advantage of potentially driving the reaction to a certain extent with reasonably high concentrations of reactants chosen at just under the threshold for spontaneous color development.

This assay is also extremely simple and suitable for use by person not skilled in veterinary or other medical or diagnostic practices and is thus very desirable for dog owners.

EXAMPLE 6

Sandwich Immunoassay for Fertility Detection

According to another embodiment of this invention a sandwich assay may be employed to detect the onset of fertility in a female dog. This assay may be performed as follows: 1 ml of urine is added to a test tube. A dipstick conjugated with Mab against the selected cLH fragment is inserted and incubated for 10 minutes. The dipstick is washed for 10 seconds under a stream of room temperature tap water, then inserted into a second test tube containing 1 ml of 1 ug/ml antibody enzyme conjugate (Mab against the carrier protein conjugated to HRP) and incubated for 5 minutes.

The dipstick is washed for 10 seconds under tap water, placed in a third test tube containing 1 ml of wash reagent for 1 minute, washed again for 10 seconds under tap water and placed in a fourth test tube containing 1 ml of TMB reagent (20 mM in 50 mM Acetate pH 5.0).

A drop (50 ul) of urea peroxide (100 mM in Acetate buffer) is added and mixed. After 5 minutes the dipstick is removed and 2 drops (100 ul) of stop reagent (100 mM Azide in Acetate buffer) is added and mixed. A blue color indicates the presence of cLH.

EXAMPLE 7

Assay for Detection of Fertility

Another assay may be performed as follows: 1 ml of urine is placed in a test tube coated with the Mab against a selected cLH fragment and incubated for 10 minutes. The contents are emptied and rinsed 5 times with tap water. Between each tap water rinse, the tube is inverted and vigorously tapped on filter paper pads to remove excess liquids. 1 ml of 1 ug/ml antibody enzyme conjugate (Mab against the carrier protein conjugated to HRP) is added and incubated for 5 minutes. The contents are emptied, rinsed with tap water, then 1 ml of wash reagent is added and incubated for 1 minute, followed by 5 rinses with tap water as noted above.

1 ml of TMB reagent (20 mM in 50 mM Acetate pH 5.0) is added and a drop (50 ul) of urea peroxide (100 mM in Acetate buffer) is added and mixed. After 5 minutes, 2 drops (100 ul) of stop reagent (100 mM Azide in acetate buffer) is added and mixed. A blue color indicates the presence of cLH.

The assays described in Examples 6 and 7 also avoid the need to prefilter urine samples. Although these formats can also drive the reaction with high reactant concentrations, they are both limited by the surface area presented for the first Mab.

1 ml of urine can be made to wet only a limited amount of surface area of these devices. This limited surface area defines the total amount of first Mab that can be included in the reaction. A 1 ml urine sample can be exposed to approximately 5 square cm in a coated test tube and even less on a dipstick. In contrast, 50 ul of 0.5% (w/v) latex particles presents greater than 25 square cm of surface, or more than 5 times the quantity of first Mab available to participate in the reaction.

EXAMPLE 8

Assay to Detect Fertility

Another embodiment of this invention may be performed as follows:

1 ml of urine, filtered through a pipet covered with a 3 um membrane, is added to a test tube followed by 1 drop (50 ul) of latex reagent (0.5% (w/v) latex particles conjugated with Mab against cLH). The contents are mixed and incubated for 10 minutes. Then 1 drop (50 ul) of antibody conjugate reagent (20 ug/ml of Mab against the carrier protein conjugated to HRP) is added, mixed and incubated for 5 minutes. The contents of the test tube are collected on a Mempore assay device (Porex), after the reactants are absorbed. 1 ml of wash reagent is added and allowed to absorb completely.

In a second test tube 5 drops (250 ul) of TMB reagent (20 mM in 50 mM Acetate, pH 5.0) is mixed with 5 drops (250 ul) of urea peroxide (20 mM in 50 mM Acetate buffer), then added to the Mempore device. After 5 minutes, 4 drops (200 ul) of stop reagent (10 mM Azide in Acetate buffer) is added. A blue color indicates the presence of cLH.

EXAMPLE 9

Assay to Detect Fertility 1 ml of urine, filtered through a pipet covered with a 3 micron membrane, is added to a Mempore assay device (Porex) imprinted with latex particles coated with Mabs against cLH fragments. After a 5 minute incubation, 2 drops of antibody conjugate reagent (20 ug/ml of Mab against the carrier protein conjugated to HRP) is added and incubated for 5 minutes. 1 ml of wash reagent is added and allowed to absorb completely. In a test tube, 5 drops (250 ul) of TMB reagent (20 mM in 50 mM Acetate, pH 5.0) is mixed with 5 drops (250 ul) of urea peroxide (20 mM in 50 mM Acetate buffer), then added to the Mempore device. After 5 minutes, 4 drops (200 ul) of stop reagent (10 mM Azide in Acetate buffer) is added. A blue color indicates the presence of cLH.

The assays described in Examples 8 and 9, while presenting a significant urine particulate problem, provide a very large effective surface area which increases the probability of binding to cLH. Example 8 allows for an increased surface area relative to Example 9 and also allows for the flexibility of longer incubation times which will not be as affected by evaporation as Example 9. Example 9, however, provides the possibility of imprinting recognizable signals such as a + or −, or dots to indicate internal positive and negative controls for comparison to the sample test area.

Numerous modifications and variations of the present invention are included in the above-identified specification and are expected to be obvious to one of skill in the art. For example, use of other appropriate Mabs and detectable labels are contemplated in the performance of this invention. Such modifications and alterations to the compositions and processes of the present invention are believed to be encompassed in the scope of the claims appended hereto.

What is claimed is:

1. A method for detecting the condition of fertility in a female canine comprising detecting the presence or absence of free or complexed metabolites of canine luteinizing hormone (LH) in the urine of the canine with the detection of said metabolites in the urine indicating the fertile period.

2. The method according to claim 1 wherein said metabolites are selected from the group consisting of one or more peptide sequences present in the protein sequence of canine LH, a protein carrier to which protein sequences of canine LH are attached, and the carrier protein/LH peptide sequence complex.

3. The method according to claim 2 wherein said peptide sequences are selected from the group consisting of the cLH sequences from amino acid 87 through 110 and the cLH sequences from amino acid 11 through 23.

4. The method according to claim 2 wherein said protein carrier is characterized by a molecular weight of approximately 100 kd, and is isolated from canine LH-rich urine by concentration on a centrifugal concentrator and elution through a Bio Gel P200 molecular sieve.

5. The method according to claim 2 wherein said detecting step comprises contacting a sample of urine from a female canine with an antibody specific for a portion of a canine LH peptide, said antibody associated with a detectable label, incubating the sample with the antibody and determining the presence or absence of antibody-antigen binding.

6. The method according to claim 5 wherein said antibody is a monoclonal antibody.

7. The method according to claim 5 wherein said label is selected from the group consisting of an enzyme system capable of generating colorimetric signals, colored latex microparticles, fluorescent compounds, radioactive compounds or elements and immunoelectrodes.

8. The method according to claim 7 wherein said label is capable of visual detection.

9. The method according to claim 8 wherein said label comprises horseradish peroxidase and tetramethyl benzidine (TMB) or alkaline phosphatase (AP) and indoxyl phosphate.

10. The method according to claim 2 wherein said detecting step comprises contacting a sample of urine from a female canine with an antibody capable of binding to a portion of said protein carrier, said antibody associated with a detectable label.

11. The method according to claim 10 wherein said antibody is a monoclonal antibody.

12. The method according to claim 10 wherein said label is selected from among the groups consisting of an enzyme system capable of generating colorimetric signals, colored latex microparticles, fluorescent compounds, radioactive compounds or elements and immunoelectrodes.

13. The method according to claim 12 wherein said label is capable of visual detection.

14. The method according to claim 13 wherein said label comprises horseradish peroxidase and TMB or AP and indoxyl phosphate.

15. The method according to claim 2 wherein said detecting step comprises contacting a sample of urine from a female canine with a first antibody specific for a first canine LH peptide and a second antibody specific for a second canine LH peptide without sterically hindering the binding of the other antibody, said first and second antibodies being associated with labels which upon interaction produce a detectable signal, incubating the sample with the first and second antibodies and determining the presence or absence of antigen-antibody binding.

16. The method according to claim 15 wherein each said antibody is a monoclonal antibody.

17. The method according to claim 15 wherein said label is selected from the group consisting of an enzyme system capable of generating colorimetric signals, fluorescent compounds, and immunoelectrodes.

18. The method according to claim 17 wherein said label is capable of visual detection.

19. The method according to claim 17 wherein said label comprises horseradish peroxidase and TMB or AP and indoxyl phosphate.

20. The method according to claim 2 wherein said detecting step comprises contacting a sample of urine from a female canine with a first antibody specific for a first canine LH peptide and second antibody specific for said protein carrier without sterically hindering the binding of the other antibody, said first and second antibodies being associated with labels which upon interaction produce a detectable signal, incubating the sample with the first and second antibodies and determining the presence or absence of antigen-antibody binding.

21. The method according to claim 20 wherein each said antibody is a monoclonal antibody.

22. The method according to claim 15 wherein said label is selected from the group consisting of an enzyme system capable of generating colorimetric signals, colored latex microparticles, fluorescent compounds, radioactive compounds or elements or immunoelectrodes.

23. The method according to claim 22 wherein said label is capable of visual detection.

24. The method according to claim 22 wherein said label comprises horseradish peroxidase and TMB or AP and indoxyl phosphate.

25. The method according to claim 15 wherein the first antibody is conjugated to a first label, said second antibody is conjugated to a second label, and the proximity of the first label to the second label upon attachment to the first and second LH peptide sequences creates a visually detectable signal.

26. The method according to claim 20 wherein the first antibody is conjugated to a first label, said second antibody is conjugated to a second label, and the proximity of the first label to the second label upon attachment to the first LH peptide sequence and said protein carrier creates a visually detectable signal.

27. The method according to claim 2 wherein said detecting step comprises exposing a urine sample to an unlabeled antibody specific for both native LH peptide and a synthetic LH peptide and (b) said synthetic peptide associated with a label, incubating the sample with the unlabeled antibody and the labeled synthetic peptide and determining the presence or absence of antigen-antibody binding, wherein the presence of native LH peptide in said urine is indicated by the absence of a detectable label, while the absence of native LH peptide in said urine is indicated by the appearance of the detectable label.

28. The method according to claim 27 wherein said antibody is a monoclonal antibody.

29. The method according to claim 2 wherein said detecting step comprises exposing a urine sample to (a) an unlabeled antibody specific for native protein carrier and a synthetic protein carrier and (b) said synthetic protein carrier associated with a label, incubating the sample with the unlabeled antibody and the labeled synthetic protein carrier and determining the presence or absence of antigen-antibody binding, wherein the presence of said native protein carrier in said urine is indicated by the absence of a detectable label, while the absence of said native protein carrier in said urine is indicated by the appearance of the detectable label.

30. The method according to claim 5 wherein said detecting step further comprises exposing said urine sample and labeled antibody to a second antibody specific for the first antibody, said second antibody associated with the same type of label, wherein the presence of LH peptide in said sample is indicated by the presence of the detectable label, amplified by the label on said second antibody.

31. The method according to claim 11 wherein said detecting step further comprises exposing said urine sample and labeled antibody to a second antibody specific for the first antibody, said second antibody associated with the same type of label, wherein the presence of carrier protein in said sample is indicated by the presence of the detectable label, amplified by the label on said second antibody.

* * * * *